(12) United States Patent
Gonzalez Cruz et al.

(10) Patent No.: US 8,013,984 B2
(45) Date of Patent: Sep. 6, 2011

(54) OPTICAL SENSOR FOR THE INSTANTANEOUS DETECTION AND IDENTIFICATION OF BIOAEROSOLS

(76) Inventors: Jorge E. Gonzalez Cruz, Santa Clara, CA (US); Alfredo Ortiz Vega, Grayson, GA (US); Victor M. Salazar Izquierdo, Madison, WI (US)

( * ) Notice: Subject to any disclaimer, the term of this patent is extended or adjusted under 35 U.S.C. 154(b) by 0 days.

(21) Appl. No.: 12/583,530

(22) Filed: Aug. 24, 2009

(65) Prior Publication Data

US 2009/0310128 A1 Dec. 17, 2009

Related U.S. Application Data

(62) Division of application No. 11/282,799, filed on Nov. 18, 2005, now Pat. No. 7,595,864.

(51) Int. Cl.
*G01N 21/00* (2006.01)

(52) U.S. Cl. .......................................... 356/73; 356/417

(58) Field of Classification Search .......... 356/317–318, 356/417, 72–73
See application file for complete search history.

(56) References Cited

U.S. PATENT DOCUMENTS

| | | | | |
|---|---|---|---|---|
| 5,681,752 | A * | 10/1997 | Prather | 436/173 |
| 5,701,012 | A * | 12/1997 | Ho | 250/461.2 |
| 5,895,922 | A * | 4/1999 | Ho | 250/492.1 |
| 5,999,250 | A * | 12/1999 | Hairston et al. | 356/73 |
| 6,532,067 | B1 * | 3/2003 | Chang et al. | 356/318 |
| 7,057,712 | B2 * | 6/2006 | Beck et al. | 356/72 |
| 2003/0207331 | A1 * | 11/2003 | Wilson et al. | 436/518 |
| 2004/0125371 | A1 * | 7/2004 | Chang et al. | 356/318 |
| 2008/0292555 | A1 * | 11/2008 | Ye et al. | 600/317 |

* cited by examiner

*Primary Examiner* — Kara E Geisel (57) ABSTRACT

A novel apparatus comprising three main systems: air sampling, detection and computerized electric system; and method of using the same in the sampling, detection and identification of bioaerosols, wherein the identification of the said bioaerosol is base on a multiphoton laser diagnostic technique along with the velocity and aerodynamic size of the particular bioaerosol. After exposing the said bioaerosols with near infrared wavelength laser, the obtained fluorescence spectra has been shown to be unique and particular for each bioaerosol, thus allowing the characterization of the said particles.

5 Claims, 6 Drawing Sheets

OPTICAL SENSOR FOR THE INSTANTANEOUS DETECTION AND IDENTIFICATION OF BIOAEROSOLS

RELATED APPLICATIONS

This application is a divisional of a U.S. patent application Ser. No. 11/282,799 filed on Nov. 18, 2005 now U.S. Pat. No. 7,595,864.

STATEMENT REGARDING FEDERALLY SPONSORED RESEARCH AND DEVELOPMENT

This invention has been sponsored at least in part by the Federal government.

FIELD OF THE INVENTION

This invention relates to the collection, detection and identification of bioaerosols and similar materials in air samples. More particularly, the invention relates to an apparatus and a process of using the said apparatus in air sampling, detection and identification of bioaereosols; wherein identification of the said aerosol is base on a multiphoton laser diagnostic technique in combination with the velocity and aerodynamic size of the particular bioaerosol.

BACKGROUND OF THE INVENTION

Biological pollutants including harmful bacteria and similar microorganisms also known as bioaerosols are pathogenic agents. These airborne microorganisms, also known as bioaerosols, may also occur naturally and may be found, for instance, in different places wherein humans have contact with animals and/or in low hygiene environmental conditions. The said bioaerosols cause diseases that are acquired by inhaling particles from particular environments. They can also be spread into the air from where they may be transmitted to new hosts. The action of the said micro-pathogens will develop a variety of serious and painful diseases that may result in the dead of the hosts. Among the vulnerable host victims of these microorganisms are mammals, including humans.

For instance the disease Psittacosis, caused by *Chlamydia psittaci* has its source in dried, powdery droppings from infected birds such as parrots and pigeons. Similarly, the Legionnaire's disease is a common form of pneumonia in older or immuno-compromised people and it can be transmitted to humans via the droplets from air-conditioning systems, water storage tanks and other water containing places wherein the bacterium *Legionella pneumophila* grows. Indeed, these microorganisms are a major cause of respiratory ailments of humans, causing allergies asthma and pathogenic infections of the respiratory tract. The said pathogenic infection may be viral or bacterial. Among important diseases affecting humans, which are transmitted person to person by inhaling airborne particles, may be caused by viruses are chickenpox, influenza, measles, and smallpox. On the other hand, examples of some airborne bacterial diseases transmitted by person to person's inhalation are Whooping cough caused by *Bordetella pertussis*, Meningitis, caused by *Neisseria* species, Diphtheria caused by *Corynebacterium diphtheriae*, Pneumonia caused by *Mycoplasma pneumoniae* and *Streptococcus species* and Tuberculosis caused by *Mycobacterium tuberculosis*.

Additionally, it is very well known that bioaerosols may be used as biological warfare, issue that in the present days has became a terrible threat to big cities everywhere in our planet. Indeed, our society is in state of alert regarding potential terrorist attacks that may involve chemical and biological agents. Possible areas that are considered targets are banks, universities, public shopping areas, public transportation centers, hospitals, and entertainment events able hold hundreds or thousand of people. These targets may be attacked by a simple act of disseminating a highly lethal biological or chemical weapon. Considering bioaerosols' characteristics: low cost, difficult detection and identification, easy dissemination, high contagious potential and the long range effects; biological agents appear to pose the greatest threat as compared with other the various methods of attack. Regardless of the origin, these microorganisms may cause multiple diseases, or medical conditions like allergies and respiratory problems that are easy to transfer to others hosts, establishing a contamination of large communities.

Unfortunately, current methods to detect and identify the said microorganisms require lengthy analysis. By the time the detection and identification of the microorganism is completed, the damage may be very extensive and the recovery extremely expensive and challenging.

The prior art discloses different methods for the detection of bioaerosol particles in gaseous sample wherein the detection system integrates spectroscopic techniques.

For instance, Carpenter et al, U.S. Pat. No. 5,254,861, discloses a system and method for the detection of the said airborne micro bio-particles wherein the particles to be detected are ionized by impacting the said particles with low energy UV radiation followed by the detection of the biological ionized particle with a detector. Carpenter's detector comprises a pair of electrically charged conducting plates placed in a parallel confronting relationship to each other.

Another example, Ho, U.S. Pat. No. 5,701,012, discloses an apparatus and a method for the detection of viable and potentially hazardous biological particles dispersed in an air stream. Ho's method comprises particle's size determination and distinguishes particles as biological from the inert non-biological particles. Ho's method comprises impacting particles with a 340 nm UV laser followed by detecting the UV emission of the particle within the particular wavelength range of approximately 400-540 nm.

Similarly, Grow U.S. Pat. No. 5,866,430, discloses a method for the identification of chemical pollutants and microorganisms. Grow's method relies on Raman spectroscopic techniques. It comprises the preparation of a complex among the analyte and a bioconcentrator, followed by exposing the said complex with a particular radiation in order to produce a Raman scattering spectrum. Detection is complete once the spectrum of the complex is collected and processed by a Raman spectrometer. Notice that the detection system and process is done base upon the complex formed and not directly from the actual specimen.

On the other hand, Stenger et al, U.S. Pat. No. 6,103,534 discloses a method for the detection of bioaerosol that comprises reaction of the bioaerosol with a chemiluminescent reagent; followed by measuring the luminescent of the mixture. Stenger's method requires very sensitive equipment made of very specific materials.

Most recently Chang et al, U.S. Pat. No. 6,532,067, discloses a method for the measurement of bioaerosols that comprises measuring size of the particle and the fluorescence spectra of single micrometer sized biological particles. Chang's method uses a light source to induce fluorescence in the UV range, preferably having 266 nm or 351 nm and does not provide a clear substantially determination of the size and velocity of the particle. Chang's velocity determination requires the simultaneous scattering of light by two different wavelengths diode lasers and the fluorescence spectra are measured only for particles falling within preset size parameters. Moreover, in Chang's method the particles are randomly dispersed in the collection and the detection steps. Clearly, the above limitations are serious disadvantages resulting from the pre-selective sensitivity and low selectivity.

Thusly, the prior art lacks to disclose in-time bioaerosol detection and accurate characterization methods that may provided a fast detection and accurate identification of the microorganism(s) in order to prevent the loss of life and minimize the extent of damage caused by harmful microorganisms. Additionally, there is a need to have better methods of air quality control and for communities to have a real sense of security in the current atmosphere of a highly probable potential for terrorist attacks.

Therefore, it is highly desirable to collect, detect and identify the bioaerosols or biological agents in a fast, efficient and accurate way.

There is a need for the quickly and accurately identification of those individuals that have been infected by a particular microorganism(s); in order to diagnose or detect human and animal diseases that can be identified by the host exhalation of air in order to treat and reduce and/or totally control, if possible, the spread of the infection. Whereby, the possible attack or contamination source is neutralized or at least drastically reduced.

SUMMARY OF THE INVENTION

The instant invention relates to a novel, real time, laser-induced multiphoton fluorescence sensor of bioaerosols and a method for the in time instantaneous collection, detection and properly characterization of a particular harmful bioaerosol(s). The novelty of the instant sensor lies in the use of in-line non-invasive techniques to measure the velocity and aerodynamic size of the biological particles presence in air samples, and inducing a multiphoton laser fluorescence emission, which is then collected in order to elucidate or characterize a given microorganism, wherein the said identification is based essentially upon the fluorescence spectrum together with the particle's velocity and aerodynamic size.

The main characteristic of the invention is the finding that each bioaerosol fluorescence spectrum induced by multiphoton radiation over a given microorganism is unique to the particular bioaerosol. Moreover, the practical aspect of using the said fluorescence spectrum obtained from a highly organized, not randomly sample is a clever fingerprint in the in-time bioaerosol characterization, increasing the selectivity and sensitivity of the complete analysis.

The instant sensor is capable of measuring particles of sizes ranging from about 0.2 to about 50 micrometers. Additionally, the sensor is build up as a compact integrated apparatus, easily deployed to any place, so its transportation is easy and saves time and efforts. Since the characterization is done fast and efficiently, the new sensor may be able to saves millions of lives of potential victims.

DETAILED DESCRIPTION OF THE INVENTION

Figure 1:
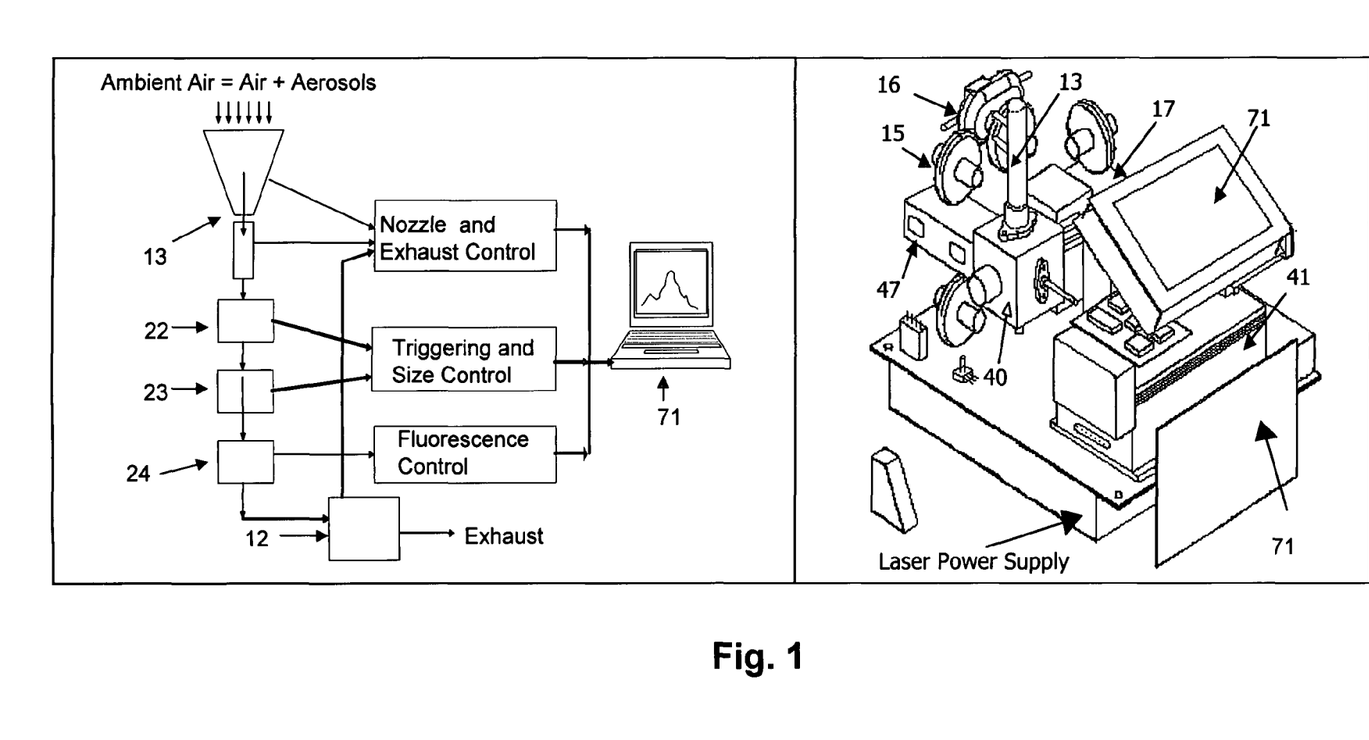
FIG. 1 Illustrates a general scheme of the preferred embodiment of the Bioaerosol Detector described herein.

Applicant's instant apparatus or sensor comprises three main components that function in an integrated manner: an air flow system (10), a detection system (40) and a computerized-electrical system (70). The integration, combination and synchronization of these three key components results in the bioaerosol detection sensor.

Figure 2:
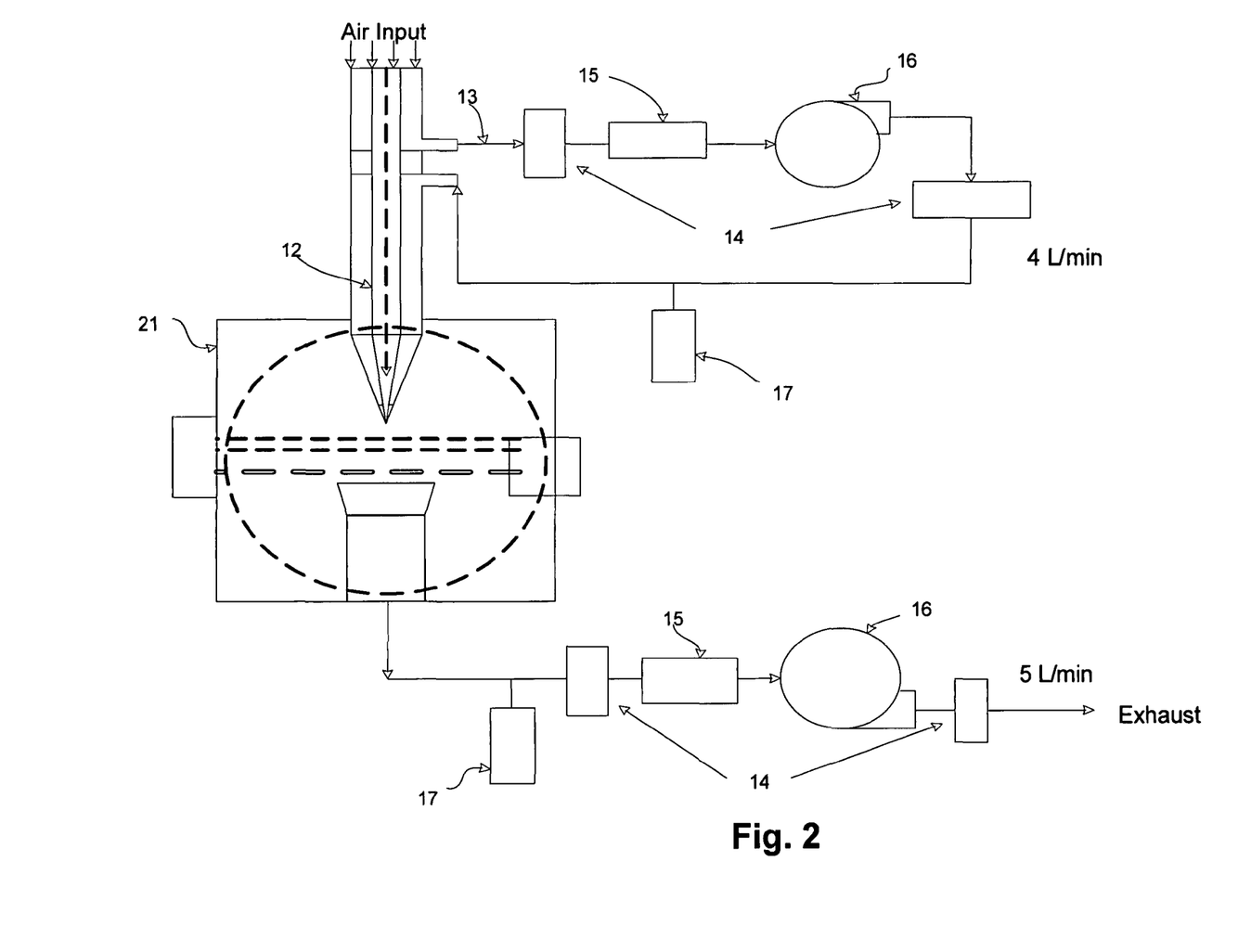
FIG. 2 Illustrates the general air flow collecting diagram described in the preferred embodiment of the invention.

The air flow system (10) comprises an air sampling system (11) and an air exhaustion system (12). The air sampling system (11) comprises a nozzle (13) and air filtering line (14) comprising air filters (15), flowmeters (16), vacuum pump (17) and pressures transducer (18).

Figure 3:
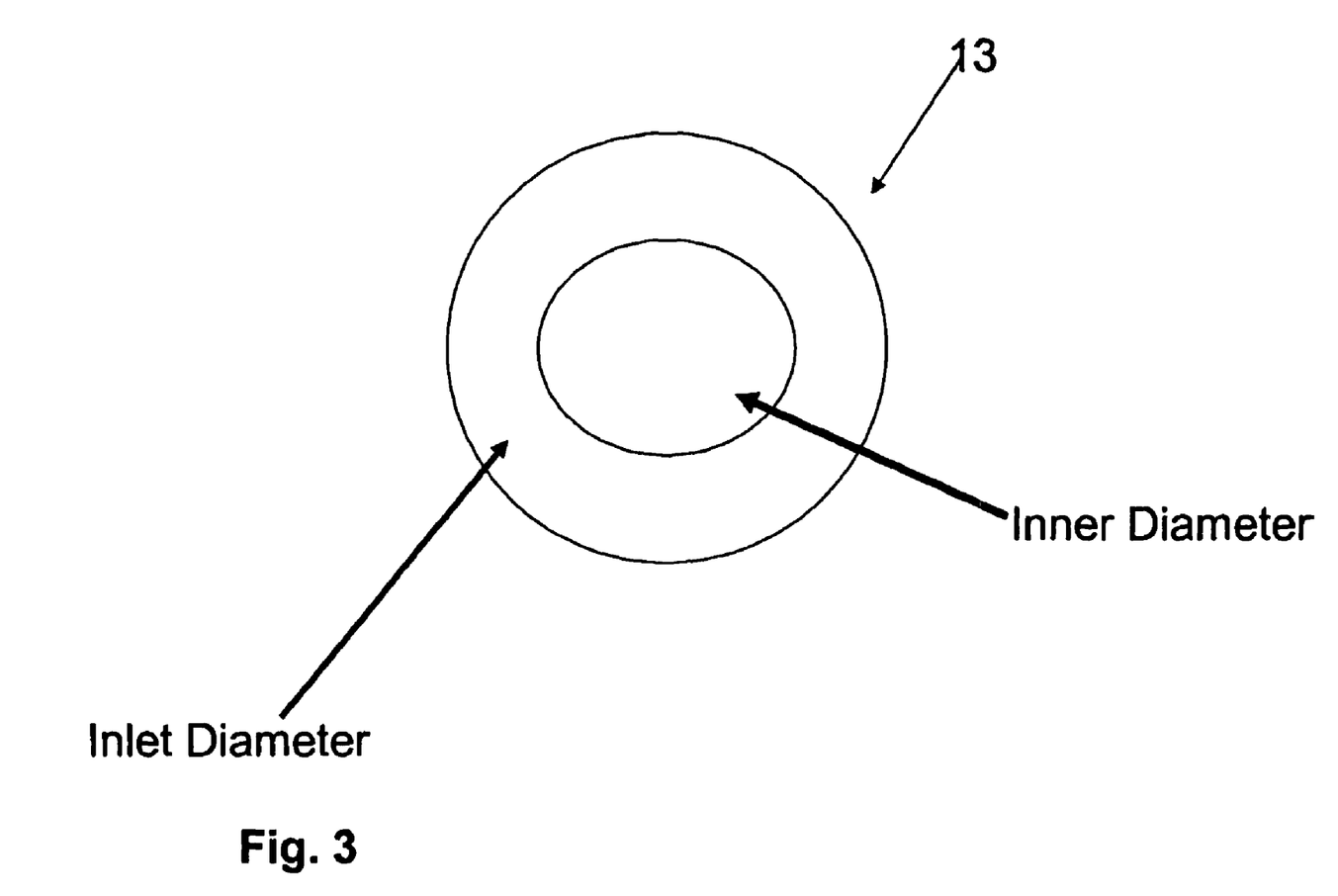
FIG. 3 Illustrates a top view of the sensor's nozzle.

Air sample is initially collected through the nozzle (13) via the air sapling system (11) at a particular rate with the help of a vacuum pump (17). Within the air flow system (11), the air flow is divided into two streams with flow rate proportions of substantially 4/1. The nozzle (13) has been designed in a particular way so, its has an inlet diameter entrance and an inner diameter entrance. Preferably, the inlet diameter is substantially 20 mm while the inner diameter is substantially 10 mm. The larger air flow rate passes through air filtering line (14), wherein clean air is generated after filtration and reintroduce to the outer part of the nozzle (13).

The design of the airflow system (11) is highly precise in order to control the particle path to and through the detection system. The design is based on typical configurations of conventional instruments used to measure aerodynamic size already commercially available.

Thus, substantially eighty percent of the collected air is passed through air sample filtering line (14). Therefore a greater air flow rate passes through a filtering process to eliminate the aerosol or any other particles and to obtain clean air. On the other hand, the remaining twenty percent air flow enters to the nozzle (12) without any filtration. The main air flow after filtration is combined with the unfiltered twenty percent air flow that contains the sample or particles to be analyzed. The said mixing of fluxes takes place preferably, previous to or in the accelerating section of the nozzle (13). In this way the filtered air flow is used as a sheath flow in order to accelerate the particles in the accelerating section of the nozzle (13) as well as it is used to dilute the air sample subjected to analysis. The net result is that the sample particles organization as one particle at a time rate proceeds from the nozzle because of a combination of the design of the nozzle. The movement of the air flows is electronically controlled by the computerized-electrical system (70). The described complete nozzle system (13) is a known design which is typical in the bio-aerosol detection devices. It is based on the description of the viscous forces described by Stokes Laws, which states that particles having the same aerodynamic size will follow the same trajectory and will allow the said particles to exceed the accelerating nozzle (13) as a string of particles in order to enter to and pass through the detection system (40) of the sensor. After the interaction of the air flow with the optical section (40), particles are exhausted to the exterior of the apparatus through the air exhaustion system that comprises pressure transducer (19), filters (20), flow meter (21) and vacuum pump (22).

Figure 4:
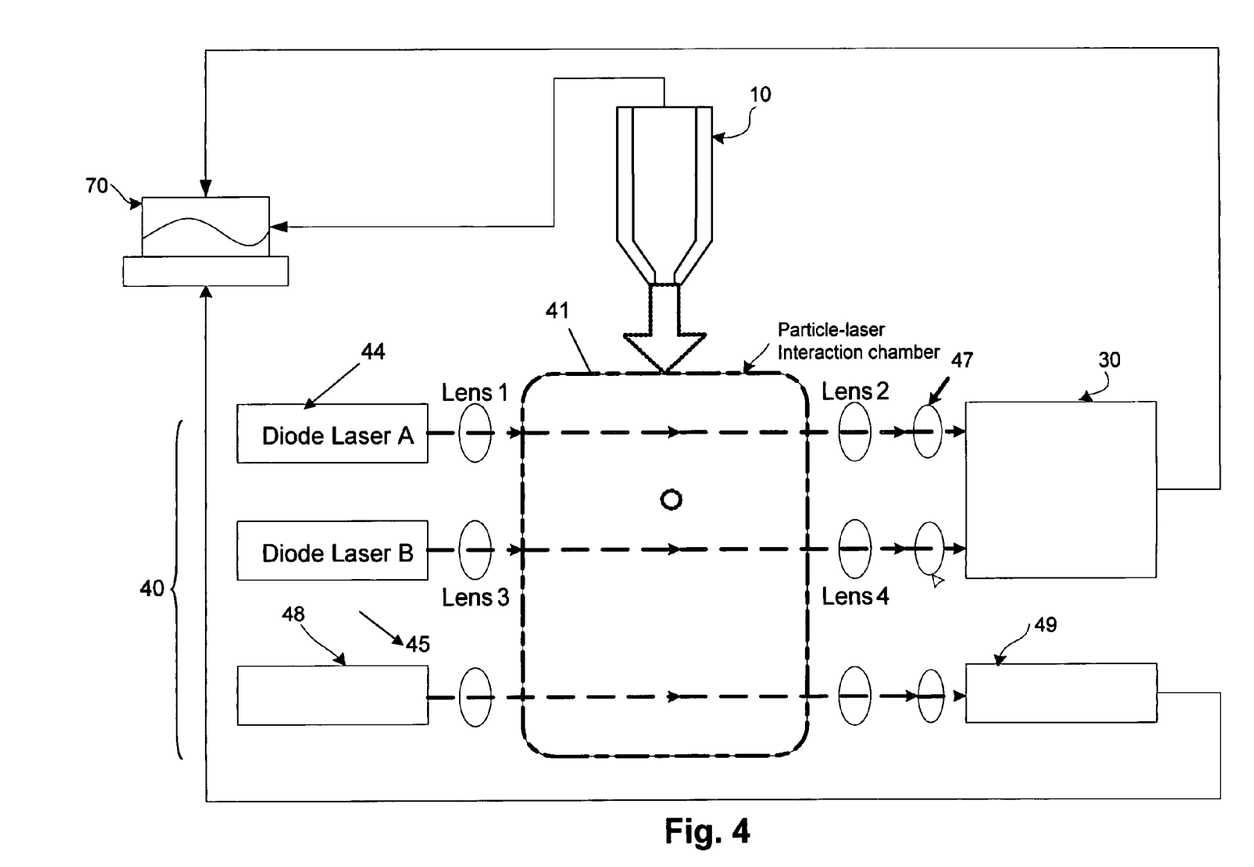
FIG. 4 Illustrates a general optical system diagram described in the preferred embodiment of the invention.

The detection section (40) of the apparatus is wherein the interaction between energy and matters takes place in the particle-laser interaction chamber (41). It comprises a triggering subsystem (22), a size subsystem (23), and a fluorescence subsystem (24).

The triggering subsystem and the size subsystem comprise laser diode A (25) and laser diode B (26) of wavelength of preferably 670 nm, together with a series of lenses (27) and a highly sensitive avalanche detector (28).

On the other hand, the fluorescence subsystem comprises a femtosecond laser (29) and a spectrometer (30).

Once the bioaerosols particles left the accelerating nozzle (13) they follow the motion of the air closely while larger particles lagged behind, increasing the relative velocity between air and particle.

In their way through the particle-light interaction chamber (41), the particles pass through the continuous beam of the laser diode A (44) initially followed by the continuous beam of the laser diode B (45). The beam-particle interactions produce scattering of the laser beam. The said light scattering due to the laser-particle interaction causes two pulses, one per each particle-beam interaction that are detected by the avalanche photodiode detector (47), and the difference in time between these two pulses which represents the time of flight is stored in the computerized system (70).

The laser diodes A (44) and B (45), are commercially available with a variety of wavelengths. The preferred ones used in the present invention have a wavelength of substantially 670 nm. The avalanche detector (47) will detect two signals from scattered light as the particle passes the continuous beams of diode lasers A (44) and B (45).

The said data is used to calculate the velocity and aerodynamic size of the particle. The detection system (40) in coordination with the electric computerized system (70) sizes the particles by measuring the velocity of the particle and correlating the velocity with a calibrated curve. The feature of increase the relative velocity is analogous to the increase in settling velocity of a particle with the same aerodynamic diameter. Thus the aerodynamic size is determined indirectly by comparison with a calibration curve previously determined using mono-dispersed spheres of known size and density.

Substantially simultaneous to the scattering from the interaction of the particle with the first of the two lasers diode (44) and (45), the highly sensitive avalanche detector (47) sends a signal to activate the shutter on the spectrometer (49).

Besides beams of the lasers A (44) and B (45), the third main light-matter interaction occurs once the particle impacts the femtosecond laser beam (48) having a wavelength of substantially 800 nm. The beam of the femtosecond laser is the source that induces a multiphoton radiation process from where the corresponding multiphoton radiation spectrum is obtained.

The said interaction results when energy from the femtosecond laser is absorbed by the bioaerosol particle producing and excitation state in the said particle. The excited particle release florescent energy that is detected by the spectrometer (49).

Figure 5:
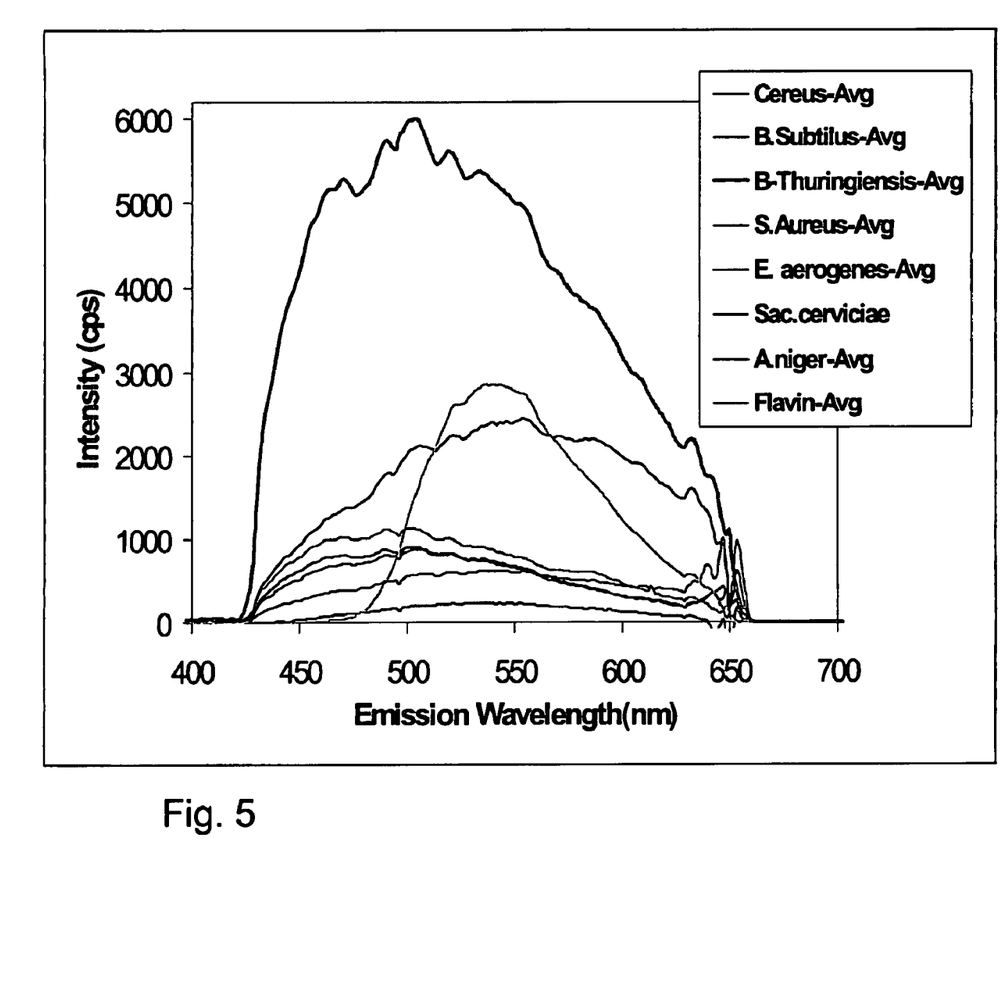
FIG. 5 Illustrates Two-photon Excited Fluorescence Spectra of Bacteria, Fungi Suspensions and Flavin Standard (left), and Standard Solutions Studied (Right).

It shall be noticed that the particular wavelength of the femtosecond laser (48) was chosen because it is known that it induce two photon excitation in biological samples, thus the particle's fluorophores would indeed absorbs two photons simultaneously, producing an excitation state in the particle. It is surprisingly found that the obtained fluorescence spectrum is very defined and clear to the point that it can be used as a particle fingerprint, as shown in Table 1 and FIG. 5.

Since the detection and characterization is directed to compact size bioaerosol particles, the model IMRA® femtosecond laser that has dimensions of 240×140×82 mm and a center wavelength of 810 nm±10 nm is the preferred femtosecond laser used in the present invention. The emitted fluorescence energy is detected by the spectrometer (49) and translated into a fluorescence spectrum by the computerized-electrical system (70). The preferred spectrometers used in the present invention among those the commercially available is the SM240 spectrometer provided by Spectral Products®; which is able to monitor wavelengths from 400 nm to 700 nm, as illustrated in FIG. 4.

Once the emitted fluorescence energy is detected by the spectrometer (49) it is translated into the particular and unique fluorescence spectrum by the computerized-electrical system (70) thus, it constitutes a central element of identification of the bioaerosol together with the velocity and aerodynamic size of the molecule. Therefore, the light-matter interaction is translated to critical data from where the particle velocity and aerodynamic size are calculated. Additionally, the second light-matter interaction based on the two photon absorption produces a unique fluorescence spectrum that in combination with the size and velocity of the particle provides a clear and reliable identification of aerosol(s).

It should be noticed that the computerized-electrical system (70) integrates all the electronic components and allows the instant sensor to work in an autonomous manner. It also collects, calculates, measures, stores, and compares data collected with a library of data for bioaerosol identification purposes. Moreover, the entire instant sensor is controlled electronically in order to insure the proper air flow conditions during the operation of the device in a variety of environmental conditions. More particularly, the computerized electronic system of the apparatus comprises the subunits: computational (71), the command interface (72), the power conversion (73) and the environmental measurement (74). These four subunits of the said system interact with spectrophotometer (30), avalanche detector (47), femtosecond laser (48) and the nozzle pumps (17) and (22) as illustrated schematically in FIG. 6.

Figure 6:
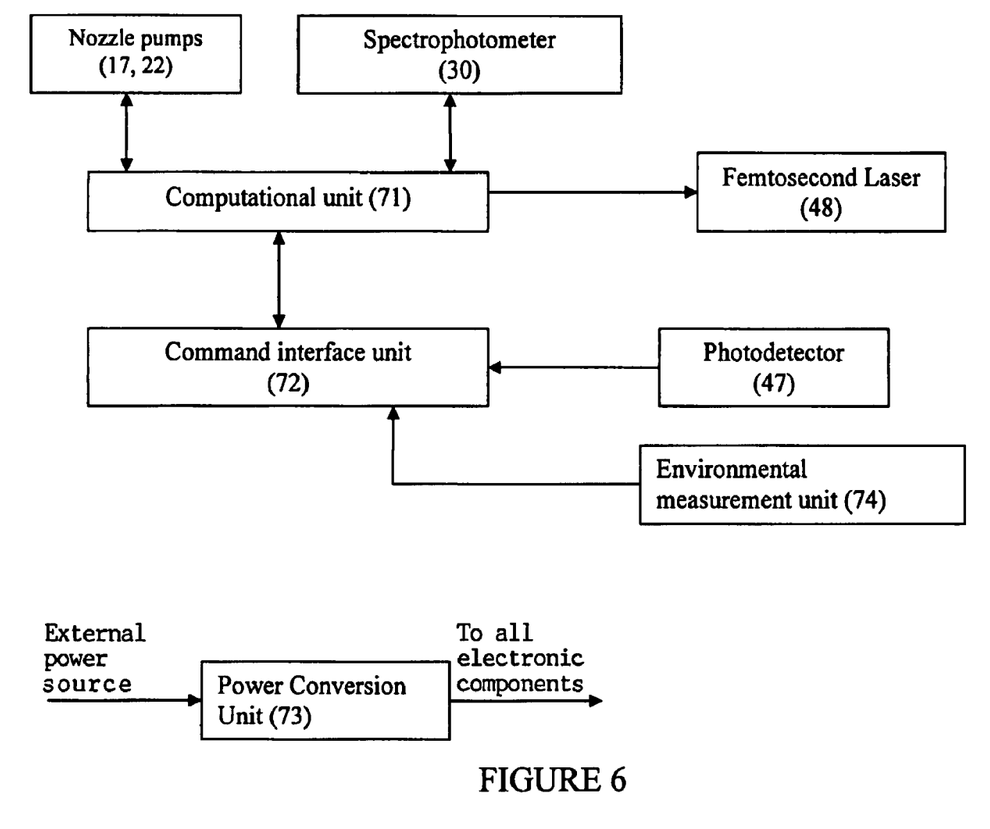
FIG. 6 Illustrates a diagram of the computerized-electrical system of the sensor.

The computational subunit (71) provides user interface facilities, including input of measurement settings and display of measurement results. It also provides a system interface to the spectrophotometer's (30) programmer's interface and data collection facilities. It also executes a program which interacts with the command interface subunit (72) to initiate one or more measurement sequences, then reads raw data from the spectrophotometer (30) and environmental data that has been collected by the command interface subunit (72) during the measurement sequence. The said data are used as inputs to the identification algorithms. The computational subunit (71) also regulates the airflow by controlling the nozzle pumps (17) and (22).

The command interface subunit (72) comprises various electronic circuits that receive inputs from the detection subsystem and produce commands to the other components of the apparatus. The primary input of the command interface subunit is the diode laser photo detector receiver, which amplifies the response of the avalanche photo detector (47) when an aerosol particle crosses the laser beams pointed at said detector. This event triggers a set of timers that count the width of said photo detector's response, and a state machine which controls several programmable delay circuits. When said delays have expired, the command interface unit (72) interrupts the computational subunit (71) in order to inform it of its need to activate the spectrophotometer (30). The command interface subunit (72) also triggers the apparatus' femtosecond laser (48). Also located in the command interface subunit (72) are the interface circuits for the apparatus' nozzle pumps (17) and (22), which are controlled by the algorithm executing in the computational subunit (71).

The final two subunits provide straightforward functionality: the power conversion unit (73) converts power from the external power source into DC power for use by the various electronic components inside the apparatus. On the other hand, the environmental measurement subunit (74) provides sensors that measure temperature, pressure and humidity external to the apparatus' housing. The outputs of these sensors are conditioned for acceptance by, and made available to, the command interface sub unit (72).

The measurement algorithm is partitioned between the state machines residing in the command interface subunit (72) and the computational subunit (71). Said algorithm comprises the following steps:

1. Wait until a particle crosses the first laser beam projected upon the avalanche photo detector (47) to trigger an event at the command interface subunit (72). Load the laser trigger delay.
2. Interrupt the computational subunit (71) so that its control program can activate the spectrophotometer (30). Load the spectrophotometer delay.
3. In parallel and independently, upon the expiration of the each of the delays described in step 2, trigger the femptosecond laser (48) and the spectrophotometer (30), respectively.
4. In parallel with steps 2 and 3, time the length of the response to the avalanche photo detector's (47) response at the command interface unit (72). Save this resulting time so it can be retrieved by the computational subunit (71).
5. The computational subunit (71) collects the time measured in step 4, and collects the data at the spectrophotometer (30). The computational unit (71) also collects the most recent environmental data that the command interface subunit (72) has retrieved from the environmental measurement subunit (74).
6. Use the time measured in step 4 and the environmental data also collected in step 4, to index into a database of known particle sizes versus spectra. Said database is created by establishing a relationship between the length of time taken by the particle to cross through the beams pointed at the avalanche photo detector (47) and its aerodynamic diameter, taking into account environmental variations. Retrieve from the database all spectra corresponding to said aerodynamic size.
7. Correlate each of the retrieve spectrum with the spectrum collected by the spectrophotometer (30). Convert each of the values of the magnitudes to the correlation peaks to a percentage of the maximum possible correlation peak.
8. Report to the user the percentages calculated in step 7.
9. If there are more particles to measure, return to step 1.

In parallel with the execution of the measurement algorithm, the computational unit (71) throttles the nozzle pumps (17) and (22) in order to maintain the flow necessary to achieve the desired design speed for the aerosol particles. The computational unit (71) receives feedback data from flow meters attached to the nozzle pump (17) and (22) lines.

Once the said emission is collected by the spectrometer, the spectrum produced by the particle and femtosecond beam interaction is compared with already saved data bank or spectrum library of known aerosol compounds.

The said data bank or spectrum library was collected by the particular method detailed below using multiphoton radiation experiments in order to excite the bioaerosol, so that the corresponding emission is induced, detected and translate to the corresponding spectra.

Multiphoton Analysis of Fungal And Bacterial Organisms

Previous works related with the identification of aerosols by measuring the fluorescence spectra are reported in the literature. However, many of these previous efforts were carried out using single photon excitation and the identification results were unclear and even confusing since in some cases different aerosols could provide identical spectrums. Surprisingly, the instant process overcomes the said inconveniences by incorporating the multiphoton induce fluorescence technique.

Multiphoton experiments using a femtosecond laser were carried out to obtain the spectra of various bioaerosols. The proposed theory that each bioaerosol has a unique multiphoton spectrum was demonstrated with these experiments using diluted solutions, and the main findings are reported.

Table 1 summarizes the two photon excited fluorescence characteristics of standard aqueous solutions of several natural fluorophores in the near infrared region. It is important to mention that two-photon excitation (2PE) fluorescence for biological imaging technique was invented in 1990 and has since been used for in vivo studies of biomolecules, as for example, in yeasts but not in live bacteria. Thus, a combination of simultaneous determining the particle size and 2PE fluorescence spectra analysis of bioaerosols makes an excellent selection for characteristics of a sensor to identify bioaerosols.

TABLE 2

Shows Two photon excited fluorescence characteristics of standard aqueous solutions of natural fluorophores in the near infrared region.

| Fluorophore | Excitation Wavelength (nm) | Emission Maximum (nm) |
|---|---|---|
| Flavins | 710-750 | 515-565 |
| Flavoprotein | 960 | 520 |
| Rivoflavin | 700-750 | 560 |
| FMN | 710-740 | 525 |
| FAD | 710-740 | 525 |
| NADH | 710-740 | 450-460 |
| NAD(P)H | 730 | 450 |

Preparation of Standards. The standards for preparation were obtained from Sigma-Aldrich Company and were used as received. Samples of these compounds were weighed and dissolved in deionized water and sonicated at room temperature to obtain nanomolar solutions for the analysis. The concentrations (mM) used for analysis were: triphosphopyridine nucleotide salt hydrate (13.1), serotonine hydrochloride (47.6), D-tyrosine (55.8), L-tryptophan methyl ester (78.5), L-tryptophan (49.0) and L-phenylalanine (61.0).

Bacteria and Fungi Suspensions. The following biological agents were prepared in Tryptic Soy Agar (TSA) culture media by the University of Puerto Rico-Mayaguez. Experimental station (Finca Alzamora) for the fungal suspensions and the Physiology Laboratory: fungi: *Saccaharomyces cerevisiae, Aspergillus niger, Trichoderma* and bacteria: *Proteus aeroginosa, Citrobacter freundii, Bacillus subtilis, Proteus vulgaris, Staphiloccocus aureus, Escherichis coli, Bacillus thuringiensis* and *Enterobacter aerogenes*. Sample preparation for analysis was as follows: biological samples were taken up with 9 inch Pasteur pipettes (repeated three times) into sterile plastic tubes and to which there was added one milliliter of deionized water with a micropipette. The resulting suspensions were sonicated for 30 minutes and analyzed for two-photon excited fluorescence spectroscopy. These samples were too dilute and did not show fluorescence emission. Therefore, these samples were then concentrated by taking twice the original amount and diluting it with one mL of deionized water and sonicating to give sufficiently concentrated samples for analysis.

Two-Photon Excited Fluorescence Studies. A Coherent Mira 900 mode-locked femtosecond laser equipped with a Niko Diaphot 300 inverted microscope and an optical power meter, was used for 2PE at 780 nm of fungal and bacterial samples. The samples were deposited onto microscope slides on an inverted microscope with capability of generating images. Each sample was re-run five times.

Steady State Fluorescence Measurements. Steady state emission spectra in the 250-700 nm range were performed using a Lambda Bio 40 spectrofluorimeter at a slit width of 2.0 nm, and a speed of 240.0 nm/min at date intervals of 1.0 nm.

Two-photon excited fluorescence spectra for the bacteria and fungi suspensions and flavin at room temperature are shown on the left side in FIG. 3. The solvent blank gave an emission maximum at 650 nm. As expected, the emission from all samples was observed in the visible region and in similar regions of emission wavelengths for the bacteria and fungi aqueous suspensions. There are differences in emission intensities and minor ones in emission maxima at similar concentrations for the bacteria and fungi samples. UV emission could be observed due to absorption by the microscope optics. The standard solutions studied showed 2PE maximum emission bands. The superimposed emission spectrum is shown on the right hand side of FIG. 3. The L-tryptophan and tryptophan methyl ester did not give any emission signal as a result of the concentration used. The phenylalanine and tryptophan did not give any signal because of the same reason. The tyrosine gave an emission band with a maximum at 650 nm. The emission spectra from the bacterial samples can be explained by 2PE of FAD and flavins upon comparison with the FAD and standard emission spectra. In addition, one-photon emission spectra with a spectrofluorometer was performed on *B. subtilis* and *proteus aeroginosa* bacteria suspensions, but did not give any emission at the specified excitation wavelength used for steady state measurements. Apparently, they need a more powerful source as that used in laser induced fluorescence. In summary, some common bacteria and fungi suspensions have been characterized from the information gathered. A unique characterization of different bacteria and fungi was obtained based on intensity at the maximum emission bands, the position of the emission band and area under these bands.

The spectrum of others aerosols were tested at a specialized laboratory. The tests showed a unique spectrum for each aerosol test using a multiphoton laser source. This validated the concept of the detection. Thus fluorescence spectra of a great amount of bioaerosols have been collected, and a spectrum database has been built and use in the instant process.

Our claim is:

1. An apparatus for the detection and the substantial identification of bioaerosols comprising:
   a) an air flow system to deliver an aligned stream of particles to an optical system;
   b) the optical system comprising a triggering subsystem and a size subsystem, wherein said triggering subsystem and said size subsystem comprise a first light emitting device aligned with a first sensitive sensor and a second light emitting device aligned with a second sensitive sensor wherein the sensor measures from the first sensitive sensor and second sensitive sensor are used to determine the velocity and the aerodynamic size of the particle by means of an electrical system for processing data and, a fluorescence subsystem comprising a third light emitting device and a fluorescent emission sensor, wherein a third light emitting device induces multiphoton fluorescent emission of said particle and wherein said fluorescent emission sensor measures the multiphoton fluorescent emission and wherein the measure of the third sensitive sensor is collected by means of said electrical system and;
   c) wherein said electrical system for processing data, comprises a library of a store data and means to process a measure data, wherein the measure data comprises the collected measures from the first sensitive sensor, the second sensitive sensor and third sensitive sensor and, wherein said electrical system integrates the air flow system and optical system by controlling the delivery of the aligned stream particles to the optical system and compares the store data with the measure data.

2. An apparatus for the detection and the substantially identification of bioaerosols as in claim 1, wherein the electrical system comprises a command interface and environmental measurement device.

3. An apparatus for the detection and the substantially identification of bioaerosols as in claim 1, wherein the air flow system comprises an air sampling system comprising a nozzle and; wherein the optical system comprises a detection chamber, wherein said nozzle has a terminal connected to the detection chamber, wherein through the said nozzle a string of said particles is delivered to the said detection chamber.

4. An apparatus for the detection and the substantially identification of bioaerosols as in claim 1, wherein the first light emitting device and second light emitting device emits light of the same wavelength and wherein the first sensitive sensor and second sensitive sensor are sensitive to light scattered by the passing particles through the emitted light from the first light emitting device and second light emitting device.

5. An apparatus for the detection and the substantially identification of bioaerosols as in claim 4, wherein the first sensitive sensor and second sensitive sensor generates generate a signal to activate the third sensitive sensor.

* * * * *